(12) United States Patent
Ahn et al.

(10) Patent No.: US 7,846,910 B2
(45) Date of Patent: Dec. 7, 2010

(54) PHARMACEUTICAL COMPOSITION, COMPOSITION FOR SCREENING THERAPEUTICS PREVENTING AND TREATING BETA AMYLOID ACCUMULATION IN BRAIN COMPRISING GCP II (GLUTAMATE CARBOXYPEPTIDASE II) AS AN ACTIVE INGREDIENT AND METHOD FOR SCREENING USING THE SAME

(75) Inventors: Sang-Mee Ahn, Kyunggi-do (KR); So Young Seo, Seoul (KR); San Sook Chae, Seoul (KR)

(73) Assignee: Korea Center for Disease Control and Prevention, Seoul (KR)

( * ) Notice: Subject to any disclaimer, the term of this patent is extended or adjusted under 35 U.S.C. 154(b) by 0 days.

(21) Appl. No.: 12/064,426

(22) PCT Filed: Aug. 23, 2006

(86) PCT No.: PCT/KR2006/003312

§ 371 (c)(1),
(2), (4) Date: Feb. 21, 2008

(87) PCT Pub. No.: WO2007/024097

PCT Pub. Date: Mar. 1, 2007

(65) Prior Publication Data

US 2008/0305099 A1 Dec. 11, 2008

(30) Foreign Application Priority Data

Aug. 23, 2005 (KR) .................... 10-2005-0077372

(51) Int. Cl.
*A61K 48/00* (2006.01)
*C12N 15/00* (2006.01)

(52) U.S. Cl. ............................. 514/44; 435/6; 435/325; 435/375

(58) Field of Classification Search ........................ None
See application file for complete search history.

(56) References Cited

FOREIGN PATENT DOCUMENTS

| WO | WO 95/09838 | 4/1995 |
|---|---|---|
| WO | WO 01/39796 | 6/2001 |
| WO | WO 03/055910 | 7/2003 |

OTHER PUBLICATIONS

SP database Acc. No. Q4609.1 from Bzdega et al, Molecular cloning of a peptidase against N-acetylaspartylglutamate from a rat hippocampal cDNA library. J Neurochem. Dec. 1997;69(6):2270-7. Alignment with SEQ ID No. 2.*
Bzdega et al, Molecular cloning of a peptidase against N-acetylaspartylglutamate from a rat hippocampal cDNA library. J Neurochem. Dec. 1997;69(6):2270-7.*
Patil et al., The AAPS Journal 2005; AAPS J. Apr. 8, 2005;7(1):E61-77.*
Pahnke et al., Neuroscience and Biobehavioral Reviews 33 (2009) 1099-1108.*
Sacha et al. Neuroscience 144 (2007) 1361-1372.*
Devlin et al., "Glutamate carboxypeptidase II: a polymorphism associated with lower levels of serum folate and hyperhomocysteinemia," *Human Molecular Genetic*, 9(19): 2837-2844 (2000).
Matsumoto et al., "Expression of human brain carboxypeptidase B, a possible cleaving enzyme for beta-amyloid precursor protein, in peripheral fluids," *Neuroscience Research*, 39(3): 313-317 (2001). Abstract Only.
Matsumoto et al., "Human brain carboxypeptidase B, which cleaves beta-amyloid peptides in vitro, is expressed in the endoplasmic reticulum of neurons," *European Journal of Neuroscience*, 13(9): 1653-1657 (2001).
Papp et al., "Expression and distribution of carboxypeptidase B in the hippocampia subregions of normal and Alzheimer's disease brain," *Acta Biol Hung*, 54(1): 55-62 (2003). Abstract Only.

* cited by examiner

*Primary Examiner*—J D Schultz
(74) *Attorney, Agent, or Firm*—Klarquist Sparkman, LLP

(57) ABSTRACT

The present invention relates to a pharmaceutical composition for the prevention and treatment for β-amyloid (Aβ) accumulation in brain comprising GCP-II (Glutamate carboxypeptidase-II) as an active ingredient, a composition for screening method of the same. GCP-II of the present invention not only degrades Aβ monomer and oligomer but also degrades soluble Aβ and insoluble Aβ, particularly aggregated Aβ, so that it can prevent the accumulation of Aβ in brain or reduce the accumulation, making it an excellent candidate for the therapeutic agent for Alzheimer's disease and Down's syndrome.

5 Claims, 11 Drawing Sheets

[Fig. 1]
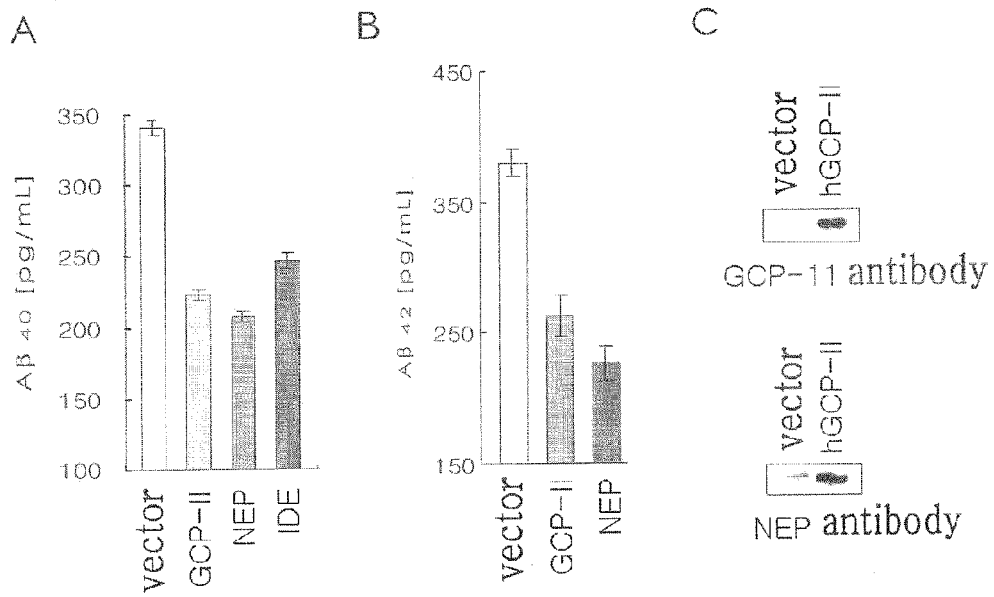
[Fig. 2]
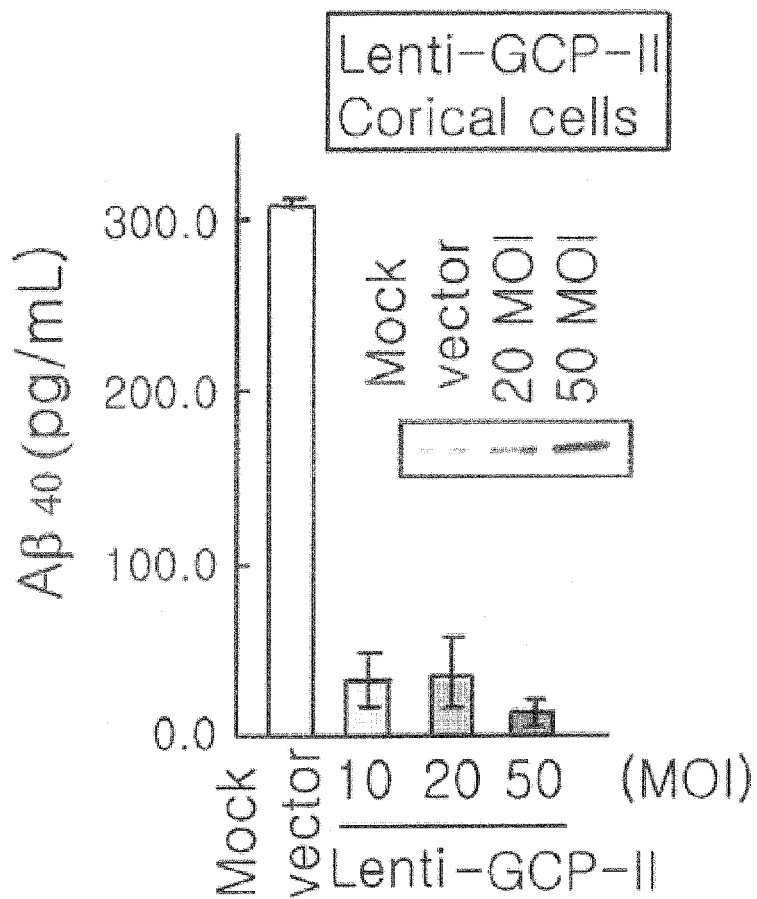

[Fig. 3]
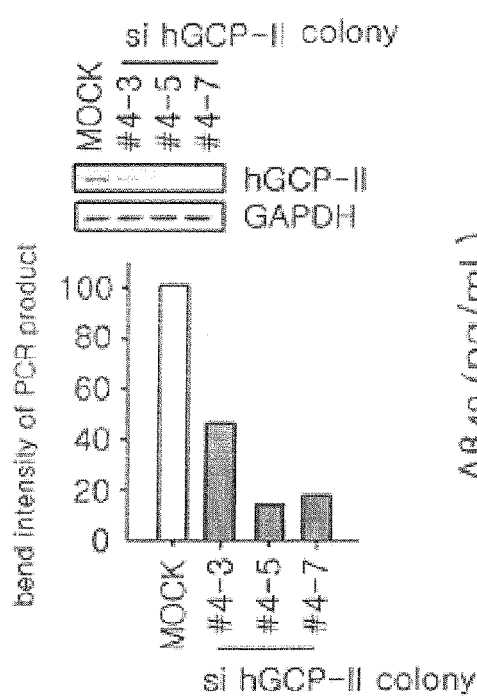 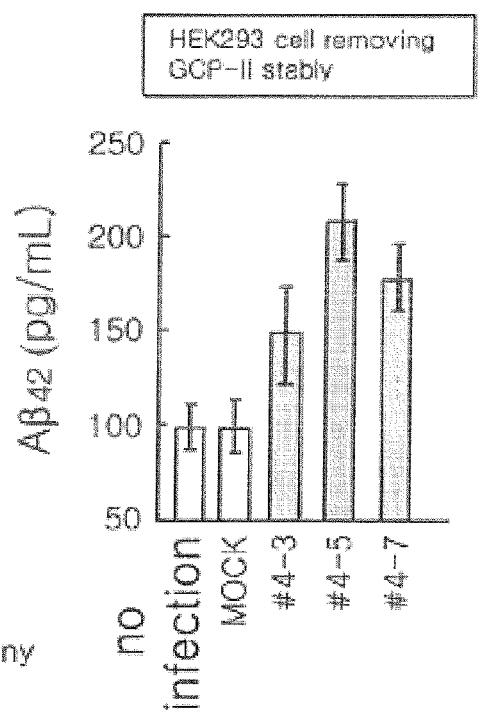

[Fig. 4]
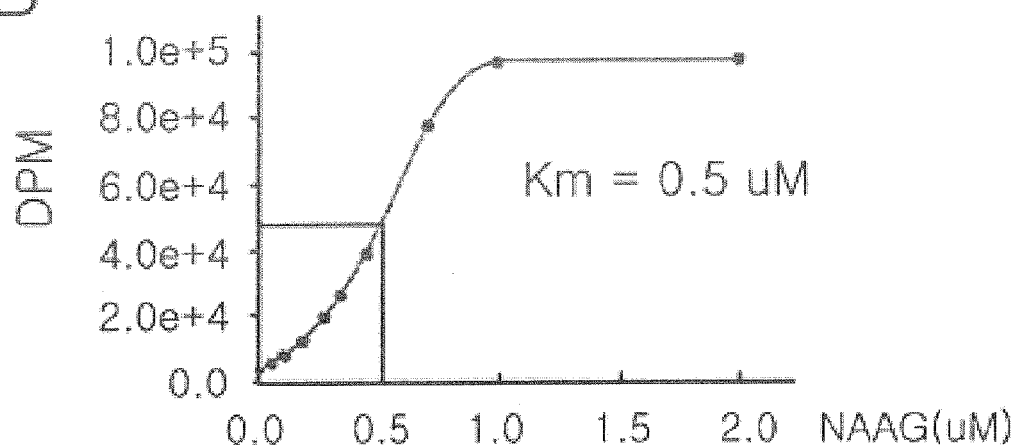

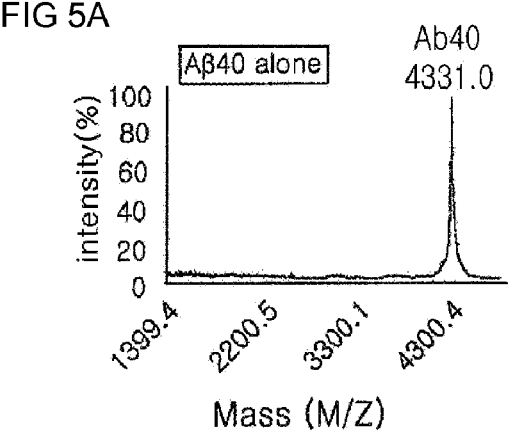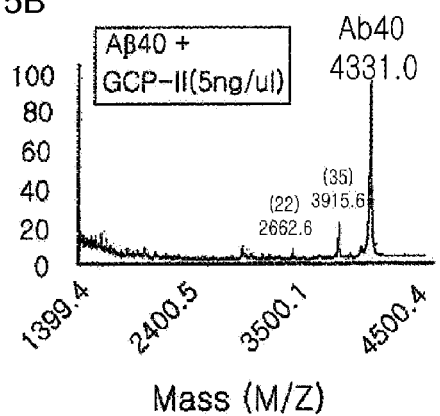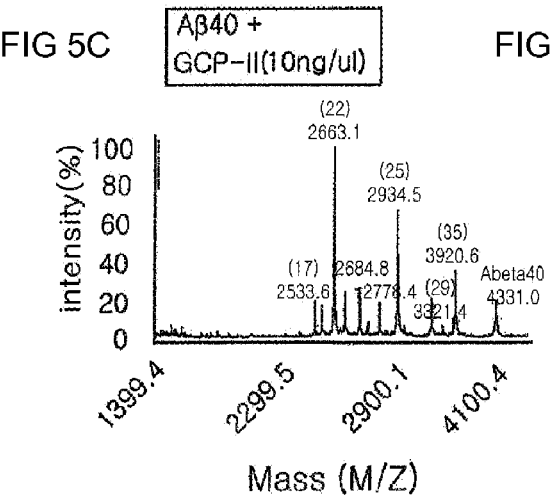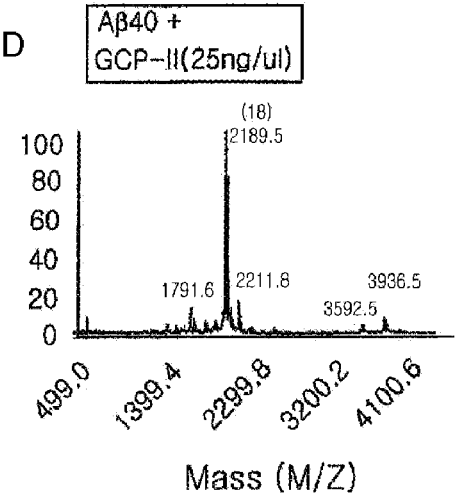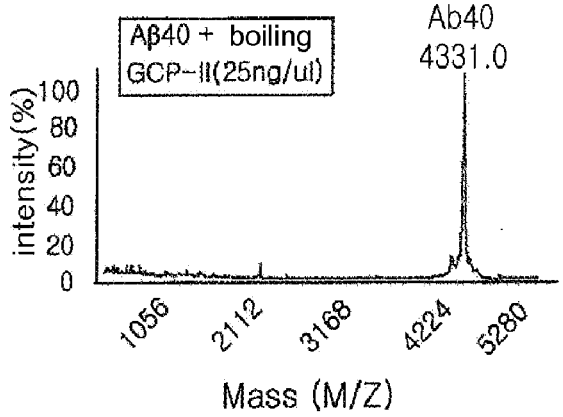

```
        18   20  22           33    35
     17 \ ↓ 19/21/              \    /
DAEFRHDSGYEVHHQKLVFFAEDVGSNKGAIIGLMVGGVV
                                    SEQ.ID.NO:7
```

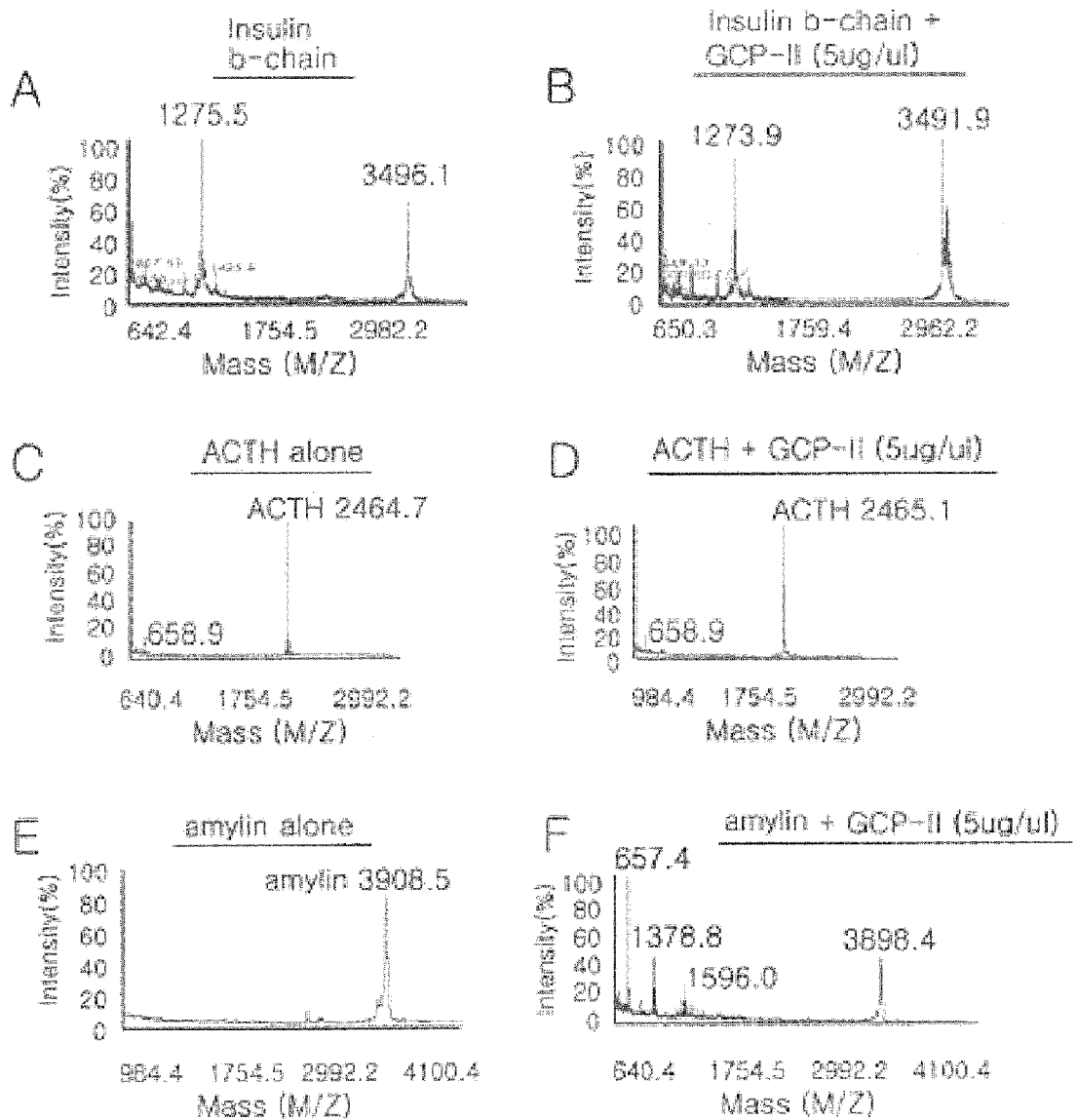
[Fig. 7]

[Fig. 8]
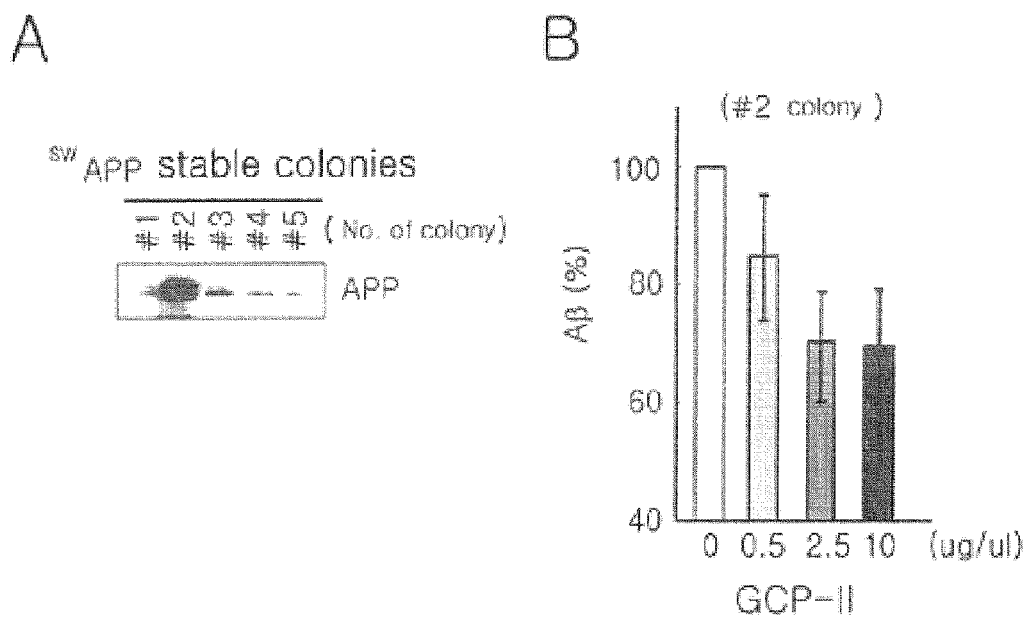

[Fig. 9]
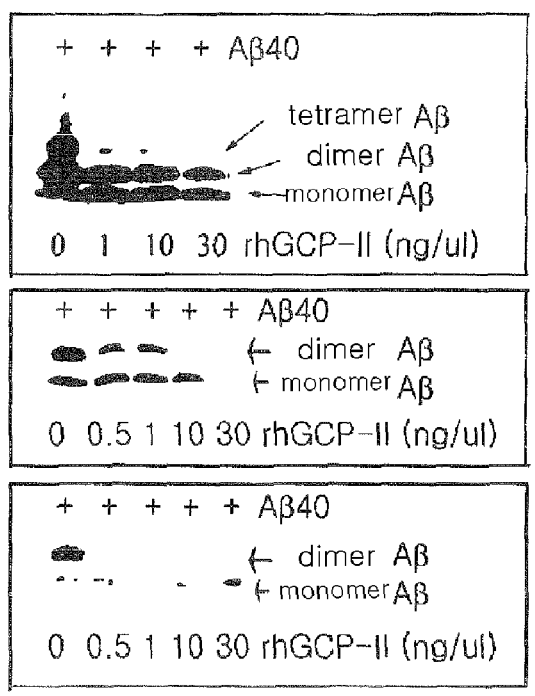
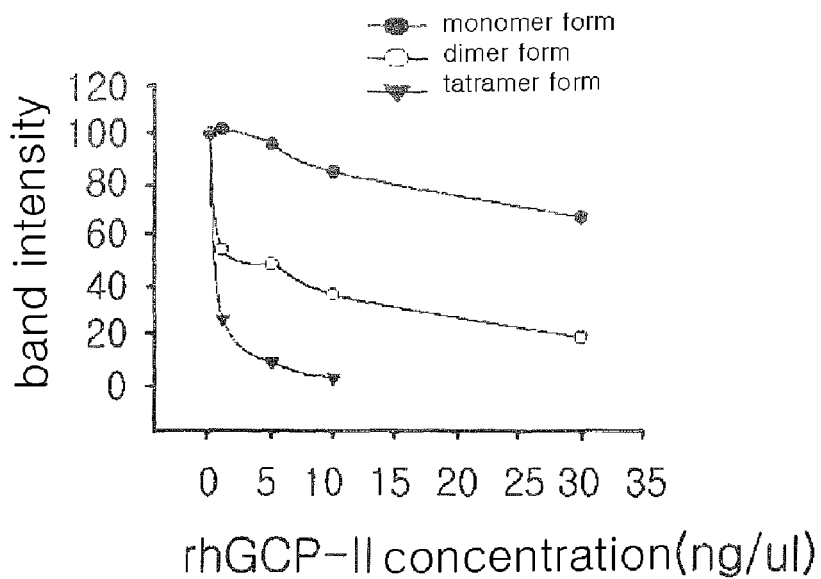

[Fig. 10]
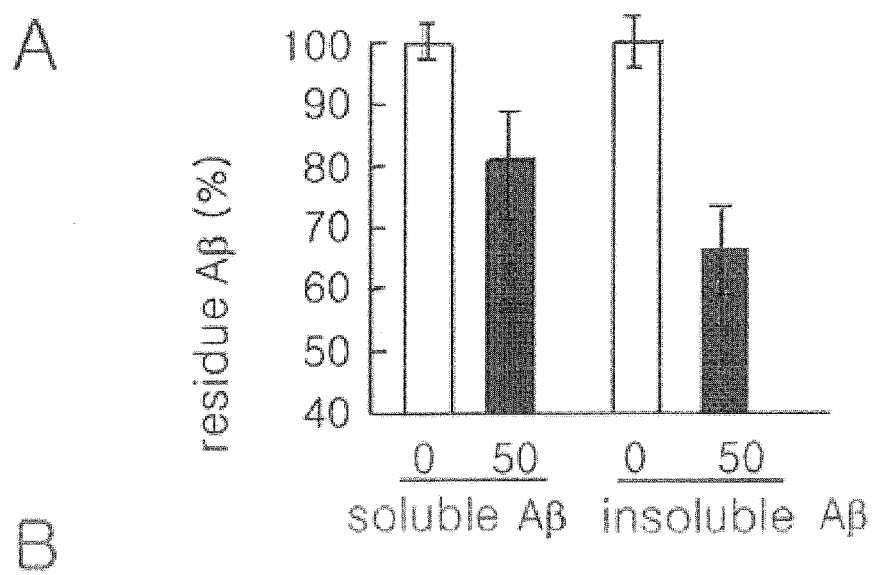

[Fig. 11]
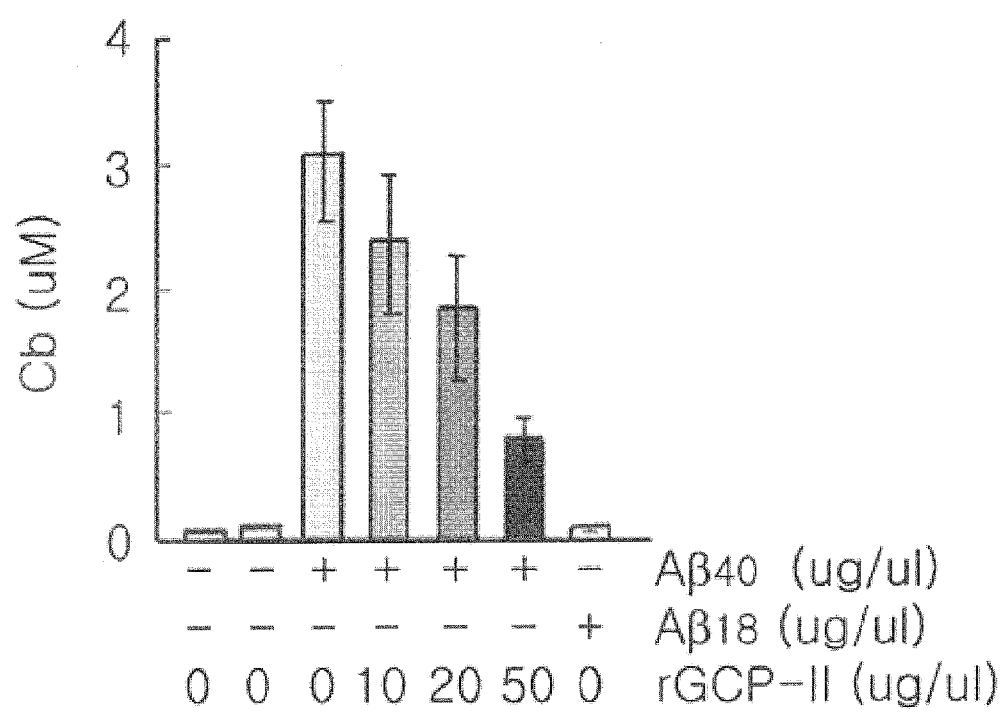

[Fig. 12]
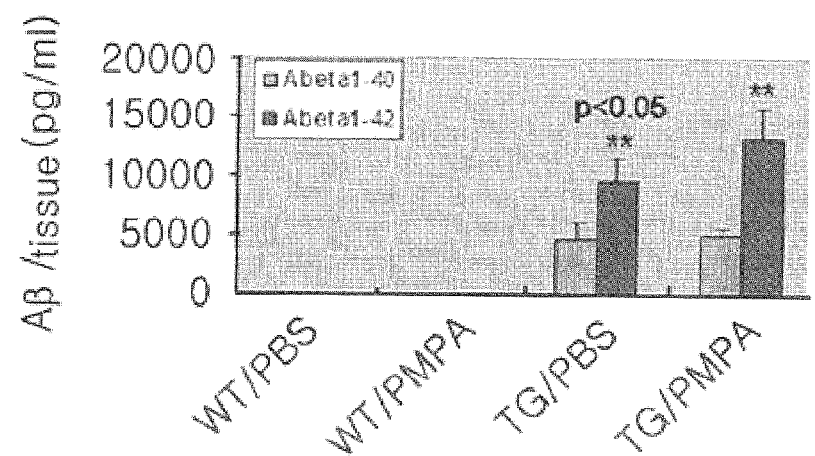
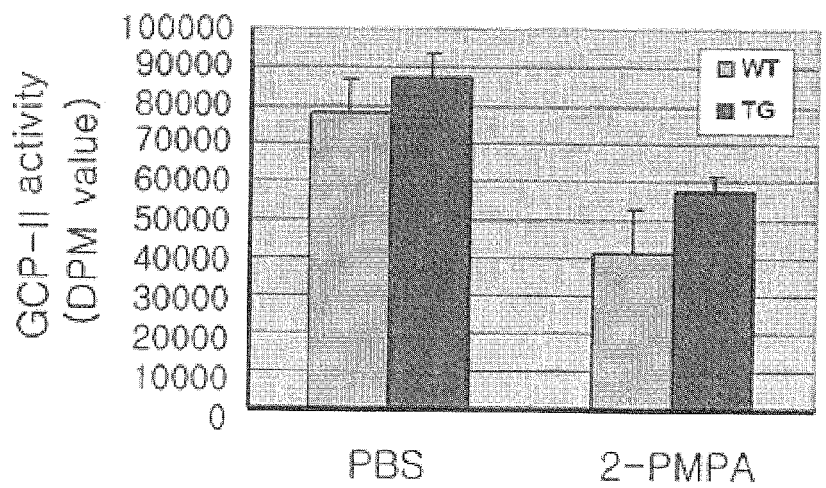

SEQUENCE LISTING

```
<160> NUMBER OF SEQ ID NOS: 7

<210> SEQ ID NO 1
<211> LENGTH: 2253
<212> TYPE: DNA
<213> ORGANISM: Homo sapiens

<400> SEQUENCE: 1
atgtggaatc tccttcacga aaccgactcg gctgtggcca ccgcgcgccg cccgcgctgg      60
ctgtgcgctg gggcgctggt gctggcgggt ggcttctttc tcctcggctt cctcttcggg     120 tggttttataa aatcctccaa tgaagctact aacattactc caaagcataa tatgaaagca     180
tttttggatg aattgaaagc tgagaacatc aagaagttct tatataattt tacacagata     240
ccacatttag caggaacaga acaaaacttt cagcttgcaa agcaaattca atcccagtgg     300
aaagaatttg gcctggattc tgttgagcta gcacattatg atgtcctgtt gtcctaccca     360
aataagactc atcccaacta catctcaata attaatgaag atggaaatga gattttcaac     420
acatcattat ttgaaccacc tcctccagga tatgaaaatg tttcggatat tgtaccacct     480
ttcagtgctt tctctcctca aggaatgcca gagggcgatc tagtgtatgt taactatgca     540
cgaactgaag acttctttaa attggaacgg gacatgaaaa tcaattgctc tgggaaaatt     600
gtaattgcca gatatgggaa agtttttcaga ggaaataagg ttaaaaatgc ccagctggca     660
ggggccaaag gagtcattct ctactccgac cctgctgact actttgctcc tggggtgaag     720
tcctatccag atgttggaa tcttcctgga ggtgtgtcc agcgtggaaa tatcctaaat     780
ctgaatggtg caggagaccc tctcacacca ggttacccag caaatgaata tgcttatagg     840
cgtggaattg cagaggctgt tggtcttcca agtattcctg ttcatccaat tggatactat     900
gatgcacaga agctcctaga aaaaatgggt ggctcagcac caccagatag cagctggaga     960
ggaagtctca aagtgcccta caatgttgga cctggcttta ctggaaactt ttctacacaa    1020
aaagtcaaga tgcacatcca ctctaccaat gaagtgacaa gaatttacaa tgtgataggt    1080
actctcagag gagcagtgga accagacaga tatgtcattc tgggaggtca ccgggactca    1140
tgggtgtttg gtggtattga ccctcagagt ggagcagctg ttgttcatga aattgtgagg    1200
agctttggaa cactgaaaaa ggaagggtgg agacctagaa gaacaatttt gtttgcaagc    1260
```

-continued

```
tgggatgcag aagaatttgg tcttcttggt tctactgagt gggcagagga gaattcaaga    1320
ctccttcaag agcgtggcgt ggcttatatt aatgctgact catctataga aggaaactac    1380
actctgagag ttgattgtac accgctgatg tacagcttgg tacacaacct aacaaaagag    1440
ctgaaaagcc ctgatgaagg cttttgaaggc aaatctcttt atgaaagttg gactaaaaaa    1500
agtccttccc cagagttcag tggcatgccc aggataagca aattgggatc tggaaatgat    1560
tttgaggtgt tcttccaacg acttggaatt gcttcaggca gagcacggta tactaaaaat    1620
tgggaaacaa acaaattcag cggctatcca ctgtatcaca gtgtctatga acatatgag    1680
ttggtggaaa agttttatga tccaatgttt aaatatcacc tcactgtggc ccaggttcga    1740
ggagggatgg tgtttgagct agccaattcc atagtgctcc cttttgattg tcgagattat    1800
gctgtagttt taagaaagta tgctgacaaa atctacagta tttctatgaa acatccacag    1860
gaaatgaaga catacagtgt atcatttgat tcactttttt ctgcagtaaa gaattttaca    1920
gaaattgctt ccaagttcag tgagagactc caggactttg acaaaagcaa cccaatagta    1980
ttaagaatga tgaatgatca actcatgttt ctggaaagag catttattga tccattaggg    2040
ttaccagaca ggcctttttta taggcatgtc atctatgctc caagcagcca caacaagtat    2100
gcaggggagt cattcccagg aatttatgat gctctgtttg atattgaaag caaagtggac    2160
ccttccaagg cctggggaga agtgaagaga cagatttatg ttgcagcctt cacagtgcag    2220
gcagctgcag agactttgag tgaagtagcc taa    2253
```

```
<210> SEQ ID NO 2
<211> LENGTH: 750
<212> TYPE: PRT
<213> ORGANISM: Homo sapiens

<400> SEQUENCE: 2

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190
```

```
Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
        210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
        290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
        450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
```

```
                 610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                    645                 650                 655

Asn Pro Ile Val Leu Arg Met Met Asn Asp Gln Leu Met Phe Leu Glu
                    660                 665                 670

Arg Ala Phe Ile Asp Pro Leu Gly Leu Pro Asp Arg Pro Phe Tyr Arg
                675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 3
<211> LENGTH: 34
<212> TYPE: DNA
<213> ORGANISM: Artificial Sequence
<220> FEATURE:
<223> OTHER INFORMATION: GCP-II-1F

<400> SEQUENCE: 3
cgcggatcca ccatgtggaa tctccttcac gaaa                            34

<210> SEQ ID NO 4
<211> LENGTH: 34
<212> TYPE: DNA
<213> ORGANISM: Artificial Sequence
<220> FEATURE:
<223> OTHER INFORMATION: GCP-II-1R

<400> SEQUENCE: 4
atttgcggcc gctggctact tcactcaaag tctc                            34

<210> SEQ ID NO 5
<211> LENGTH: 34
<212> TYPE: DNA
<213> ORGANISM: Artificial Sequence
<220> FEATURE:
<223> OTHER INFORMATION: GCP-II-2F

<400> SEQUENCE: 5
cgcagatcta ccatgtggaa tctccttcac gaaa                            34

<210> SEQ ID NO 6
<211> LENGTH: 34
<212> TYPE: DNA
<213> ORGANISM: Artificial Sequence
<220> FEATURE:
<223> OTHER INFORMATION: GCP-II-2R

<400> SEQUENCE: 6
atttagatct ttaggctact tcactcaaag tctc                            34

<210> SEQ ID NO 7
<211> LENGTH: 40
<212> TYPE: PRT
<213> ORGANISM: Artificial Sequence
```

```
-continued

<220> FEATURE:
<223> OTHER INFORMATION: the degradation site of Amyloid beta by rGCP-II

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40
```

PHARMACEUTICAL COMPOSITION, COMPOSITION FOR SCREENING THERAPEUTICS PREVENTING AND TREATING BETA AMYLOID ACCUMULATION IN BRAIN COMPRISING GCP II (GLUTAMATE CARBOXYPEPTIDASE II) AS AN ACTIVE INGREDIENT AND METHOD FOR SCREENING USING THE SAME

CROSS REFERENCE TO RELATED APPLICATIONS

This is the U.S. §371 National Stage of copending International Application No. PCT/KR2006/003312, filed Aug. 23, 2006, published in English under PCT Article 21(2), which in turn claims the benefit of Korean Patent Application No. 10-2005-0077372, filed Aug. 23, 2005.

TECHNICAL FIELD

The present invention relates to a pharmaceutical composition and a composition for screening the therapeutics preventing and treating the accumulation of β-amyloid (referred as 'Aβ' hereinafter) in brain which contains GCP-II (glutamate carboxypeptidase-II) as an active ingredient and a screening method using the same.

BACKGROUND ART

With sky-rocketing economic growth in Korea, senile dementia represented by Alzheimer's disease has been a social problem with the increase of the aged population. Today the Alzheimer's disease becomes more serious social and economical burden day by day.

Alzheimer's disease (referred as 'AD' hereinafter) is the most dominant neurodegenerative disease caused by the pathological accumulation of Aβ in brain. The unbalance between Aβ synthesis and its elimination results in the accumulation of Aβ and senile plaques (Geula C. et al., Nat. Med., 4, 827-831, (1998)). Alzheimer's dementia is divided into familial AD (FAD) attributed to genetic mutation and sporadic AD (SAD) whose causes have not been explained yet. The FAD patients took 5-10% of the total AD patients and the rest are sporadic AD patients. The causative genes for familial AD have been identified to be presenilin 1 (referred as 'PS1' hereinafter) on chromosome 14, amyloid precursor protein (referred as 'APP' hereinafter) on chromosome 21 and presenilin 2 (referred as 'PS2' hereinafter) on chromosome 1.

In the APP over-expressing transgenic mice, more precisely in transgenic mice over-expressing mutated ATT gene which is very common in familial AD patients, senile plaques were observed and space perception was decreased, which are characteristic symptoms of AD patients. When normal PS1 protein was over-expressed, Aβ generation was not changed. However, in transgenic mice over-expressing mutated PS1 protein, plenty of Aβ were generated as shown in AD patients. Considering all the earlier reports, APP mutation observed in FAD patients seems to be closely related to over-production of Aβ and further responsible for AD break-out.

While studies on APP, PS1 and PS2 genes involved in overproduction of Aβ in familial AD patients have been actively progressed, studies on the effect of the reduced Aβ degradation according to aging have been unsatisfactory. In recent cell- or animal tests, it was confirmed that inhibiting the activity of neprilysin (referred as 'NEP' hereinafter) or insulin degrading enzyme (referred as 'IDE' hereinafter) results in the over-accumulation of Aβ suggesting that the decrease of the expression and functions of Aβ degrading gene might be the major cause of Aβ accumulation in aged brain. NEP or IDE mediated Aβ degradation was observed in the mouse produced by crossbreeding a transgenic mouse over-expressing NEP or IDE with a mouse over-generating Aβ.

The activation of enzymes degrading Aβ might contribute to the treatment of AD including familial AD since they can degrade Aβ whose level increases according to aging. However, it is controversial whether these proteases can degrade condensed Aβ as well. Even in a transgenic mouse over-expressing these proteases, Aβ level was still high, indicating that there is another protease which can decompose Aβ.

Various attempts have been made so far to prevent and treat AD. For example, a non-self antigen vaccine based on Aβ peptide has been used to inhibit Aβ agglutination or accumulation (WO 2001/39796), an Aβ isolating compound based on VEGF polypeptide has been used to inhibit the combination of VEGF with Aβ (WO 2003/055910), a compound inhibiting Aβ core protein generation and plaque formation based on the compound used for the treatment of Down's syndrome and senile dementia has been used for the treatment of AD (WO 1995/09838).

The present inventors have been tried to identify an enzyme which is able to degrade Aβ and have been applied for a patent with a protein inhibiting Aβ agglutination isolated from bacteria (Korean Patent Publication No. 10-2005-000007102).

As an effort to find out an enzyme degrading Aβ among human proteins, the present inventors have searched a candidate among human endogenous proteins having similar sequence with AABA (amyloid peptide aggregation blocking activity), an Aβ degrading protein, and at last selected GCP-II as a promising candidate and further examined its biological and biochemical properties. As a result, the present inventors completed this invention by confirming that the GCP-II is able to degrade not only Aβ in monomer or oligomer form but also aggregated Aβ or even Aβ in soluble, insoluble form.

DISCLOSURE OF INVENTION

Technical Problem

It is an object of the present invention to provide a pharmaceutical composition and a composition for screening the therapeutics preventing and treating the accumulation of Aβ in brain which contains GCP-II as an active ingredient and a screening method using the same.

Technical Solution

To achieve the above object, the present invention provides a pharmaceutical composition for the prevention and treatment of Aβ accumulation in brain containing GCP-II protein as an active ingredient.

The present invention also provides a composition for screening the therapeutics preventing and treating the accumulation of Aβ in brain which contains GCP-II gene as an active ingredient.

The present invention further provides a composition for screening the therapeutics preventing and treating the accumulation of Aβ in brain which contains GCP-II protein as an active ingredient The present invention also provides a screening method for the therapeutics preventing and treating the accumulation of Aβ in brain comprising the following steps:

i) Contacting the composition containing the GCP-II gene with a test subject; and ii) Determining whether the composition can increase or inhibit the expression of the gene by observing the reaction of the above step i).

The present invention also provides a screening method for the therapeutics preventing and treating the accumulation of Aβ in brain comprising the following steps:

i) Contacting the composition containing the GCP-II protein with a test subject; and ii) Determining whether the composition can increase or inhibit the expression of the gene by observing the reaction of the above step i).

The present invention also provides a preventive and therapeutic agent for Aβ accumulation in brain containing a GCP-II gene expression vector as an active ingredient.

Hereinafter, the present invention is described in detail.

The present invention provides a pharmaceutical composition for the prevention and treatment of Aβ accumulation in brain containing GCP-II protein as an active ingredient.

The present inventors have separated an aminopeptidase from *Streptomyces* sp. having the activity of reducing the aggregation of amyloid peptide by Congo red assay. The separated protein was named 'ABBA (amyloid peptide aggregation blocking activity)' and is described in Korean Patent Publication No. 10-2005-000007102.

The present inventors also found out various mammalian aminopeptidases having high homology with ABBA separated from *Streptomyces* sp. from searching the human genome database. One of those aminopeptidases is human GCP-II having the carboxypeptidase activity.

GCP-II is a transmembrane metalloproteinase expressed in many human organs and plays a role in changing folate taken-in from a diet into an absorbable form (Halsted et al., 1998, J. Biol. Chem., 273, 20417-24; Ghosh et al., 2003, Prostate, 57, 140-151). GCP-II has been known to be involved in the formation of glutamate from NAAG (N-acetyl aspartyl glutamate), a glutamate neurotransmitter precursor, in brain of an ischemic disease patient, which is still controversial, though. For instance, GCP-II knockout mice generated in two different labs of two different countries exhibited different results; the death of fetus (Tsai et al., 2003, Synapse, 285-92, 2003) or no change (Bacich et al., 2002, J. Neurochem., 83, 20-9). So, the concrete physiological functions of GCP-II in brain have not been explained, yet. Nevertheless, the administration of GCP-II inhibitor into a stroke model mouse results in the decrease of cell death in brain, suggesting that over-production of glutamate by GCP-II might have a harmful effect on nerve cells (Slusher et al., Nat. Med. 5, 1396-402, 1999; and Tortella et al., Eur. J. Pharmacol., 402, 31-7, 2000).

To investigate the Aβ degradation by GCP-II, synthetic $A\beta_{40}$ (FIG. 1A) or $A\beta_{42}$ (FIG. 1B) was added to the cell culture solution containing HEK293 cells over-expressing GCP-II and HEK293 cells over-expressing NEP and IDE which are known as Aβ degrading enzymes. After reaction, the level of Aβ in the medium was measured by ELISA. As a result, the levels of $A\beta_{40}$ and $A\beta_{42}$ in the cell culture medium containing GCP-II over-expressing cells were 30% decreased, compared with those in the cell culture medium containing cells transfected with a mock vector, indicating that GCP-II has similar effect on Aβ degradation with NEP or IDE.

To investigate whether Aβ degradation effect of GCP-II was still observed in cortical cells or not, GCP-II was over-expressed in primary cortical cells by using lenti-virus, and then the level of Aβ degradation was investigated. As a result, GCP-II degraded Aβ more than 90% in primary cortical cells, suggesting that GCP-II acts effectively to degrade Aβ in primary cortical cells where Aβ is actually accumulated (FIG. 2).

It was further investigated whether GCP-II could degrade synthetic Aβ in vivo as it did in cultured cells over-expressing GCP-II. Synthetic Aβ was added to cells in which GCP-II expression was blocked by using siRNA, followed by ELISA to measure the remaining Aβ in the medium. And the result was compared with the post-experimental level of Aβ in those cells expressing GCP-II containing an empty vector. As a result, Aβ degradation affected by siRNA was reduced, compared with that of a control, suggesting that GCP-II can lower the level of physiologically generated Aβ (FIG. 3).

To conform whether GCP-II can actually degrade over-expressing Aβ in vivo, the present inventors investigated Aβ degradation capacity by GCP-II inhibitor in a transgenic mouse over-expressing Aβ and as a result, the mice treated with the GCP-II inhibitor was significantly degrade about 50% in wild type mouse and about 30% in transgenic mouse.

To determine which amino acid site of Aβ was cleaved by GCP-II, a recombinant GCP-II protein (referred as 'rGCP-II' hereinafter) was constructed (FIG. 4A) to measure the enzyme activity (FIG. 4B). Aβ and the Aβ reacted with rGCP-II protein were examined by MALDI-TOF to identify the degraded peptide (FIGS. 5A-D). Further, GCP-II lacking of its protein activity, resulted in no degradation of Aβ, proving that Aβ degradation is due to GCP-II enzyme activity of GCP-II (FIG. 5E). The Aβ degradation products analysed from MALDI-TOF assay were $A\beta_{18}$, $A\beta_{19}$, $A\beta_{20}$, $A\beta_{21}$, $A\beta_{22}$, $A\beta_{25}$, $A\beta_{29}$ and $A\beta_{35}$ fragments. In particular, $A\beta1_{-18}$ was confirmed to be a major degraded fragment by rhGCP-II (FIG. 6).

To confirm that GCP-II degrades Aβ specifically, GCP-II was reacted with amylin, ACTH (adrenocorticotropic hormone) and insulin β-chain, followed by measuring molecular weight of each sample with a molecular weight analyzer. As a result, insulin β-chain (FIGS. 7A and 7B) and ACTH (FIGS. 7C and 7D) were not degraded by GCP-II, whereas amylin exhibited two peaks at 1500 and 2000 (FIGS. 7E and 7F). From the above result, the present inventors determined that GCP-II has a substrate specificity to amylodoigenic proteins such as Aβ or amylin. According to a previous report, IDE can degrade amylin, too (Benette et al., J. Biol. Chem., 275, 36621-5, 2000). Amylin degradation by GCP-II means that GCP-II is a crucial enzyme which degrades a substrate having aggregation toxicity.

In addition to the effect of GCP-II on synthetic Aβ the degradation effect on endogenous Aβ was investigated. HEK293 cell line stably expressing $^{sw}$APP (Swedish mutant APP) gene and thus over-producing Aβ was prepared. The medium was recovered and reacted with rGCP-II protein, and then non-reacted Aβ remaining in the medium was quantified by ELISA. Aβ in the medium of HEK293 cells stably expressing $^{sw}$APP was reacted with different concentrations of rGCP-II and as a result, the level of endogenous $A\beta_{42}$ was reduced, suggesting that rGCP-II degrades endogenous Aβ as well (FIG. 8).

The degradation effect of GCP-II on Aβ monomers and multimers was also investigated. Aβ aged for 7 days was reacted with rGCP-II, then, the resulting Aβ was analysed by western blotting. As a result, when Aβ was reacted with rGCP-II with increasing the concentration of rGCP-II, it was multimers (oligomers) rather than monomers who could be degraded fast. From the result, it was confirmed that GCP-II is capable of degrading Aβ in oligomer form which is harmful to nerve cells.

To investigate whether human GCP-II could easily degrade various Aβ$_{40}$ forms, Aβ was fractionated into soluble and insoluble forms and the fractions were co-cultured with rGCP-II. As a result, rGCP-II reduced insoluble Aβ$_{40}$ by 35%, while it reduced soluble Aβ$_{40}$ by 20% (FIG. 10A). From the above results, it was confirmed that GCP-II of the present invention has a degradation activity even to the insoluble Aβ, suggesting that GCP-II of the invention can efficiently degrade the accumulated Aβ (FIG. 10B).

The degradation effect of rGCP-II on the aggregated Aβ was investigated. Aβ aggregated for 21 days was reacted with rGCP-II protein, followed by quantification by Congo red assay. As a result, Aβ fragments being apart from the aggregation core sequence were observed, indicating that Aβ was degraded by rGCP-II. Therefore, GCP-II of the invention can efficiently degrade various forms of Aβ especially the aggregated Aβ which is supported by the founding that Cb value was reduced in proportion to the concentration of GCP-II (FIG. 11).

The composition of the present invention containing GCP-II protein as an active ingredient can additionally include a pharmaceutically acceptable and physiologically permissible juvantia. As a juvantia, excipients, disintegrating agents, sweetening agents, binders, coating agents, inflating agents, lubricants, glidants or solubilising agents such as flavors can be used.

The composition of the present invention containing GCP-II protein as an active ingredient can also include, in addition to the above-mentioned effective ingredients, one or more pharmaceutically acceptable carriers for the administration. A pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following a method represented in Remington's Pharmaceutical Science (the newest edition), Mack Publishing Company, Easton, Pa.

The formulations for the composition of the invention containing GCP-II protein as an active ingredient are granules, powders, coated tablets, pills, capsules, suppositories, syrups, juice, suspensions, emulsions, drops or injectable solutions and sustained released formulations.

The composition of the present invention containing GCP-II protein as an active ingredient can be administered orally or parenterally (for example, intravenous, intraarterial, intramuscular, intrasternal, percutaneous, intranasal, inhalation, hypodermic, local or peritoneal injection). The effective dosage of the composition can be determined according to weight, age, gender, health condition, diet, administration frequency, administration method, excretion and severity of a disease. The dosage of the composition of the invention is preferably 0.1□/kg~0.1 g/kg per day. Administration frequency is once a day or preferably a few times a day.

The composition of the present invention can be administered singly or treated along with surgical operation, hormone therapy, chemotherapy and biological reaction regulator, to treat AD.

The present invention also provides a composition for screening a preventive and therapeutic agent for Aβ accumulation in brain containing human GCP-II gene.

The human GCP-II gene can include one or more nucleotide sequences selected from a group consisting of nucleotide sequence represented by SEQ. ID. NO: 1, nucleotide sequence including polymorphism of the sequence represented by SEQ. ID. NO: 1 or the nucleotide sequence of a gene fragment containing the polymorphism.

The present invention further provides a composition for screening a preventive and therapeutic agent for Aβ accumulation in brain containing GCP-II protein.

The GCP-II protein can include one or more amino acid sequences selected from a group consisting of amino acid sequence represented by SEQ. ID. NO: 2, a protein expressed from a nucleotide sequence represented by SEQ. ID. NO: 1 or a nucleotide sequence including polymorphism of the sequence represented by SEQ. ID. NO: 1 and a GCP-II polypeptide fragment exhibiting equal physiological activity with GCP-II.

The present invention also provides a screening method for the therapeutics preventing and treating the accumulation of Aβ in brain comprising the following steps:
  i) Contacting the composition containing the GCP-II gene with a test subject; and
  ii) Determining whether the composition can increase or inhibit the expression of the gene by observing the reaction of the above step i).

The present invention also provides a screening method for the therapeutics preventing and treating the accumulation of Aβ in brain comprising the following steps:
  i) Contacting the composition containing the GCP-II protein with a test subject; and
  ii) Determining whether the composition can increase or inhibit the expression of the gene by observing the reaction of the above step i).

According to the screening method of the invention, the confirmation of the reaction between a composition containing GCP-II gene and a test subject can be performed by the conventional methods used for confirming the reaction between DNA-DNA, DNA-RNA, DNA-protein and DNA-compound.

For example, in vitro hybridization assay examining the linkage of the above gene to a test subject, Northern blot assay performed after the reaction between mammalian cells and a test subject, quantitative PCR and quantitative real time PCR can be hired to measure the expression rate of the gene. In addition, the gene is linked to a reporter gene, which was then introduced into a cell to be reacted with a test subject and then the expression rate of the reporter protein was measured.

A composition of the present invention can additionally include distilled water or a buffer to maintain the nucleic acid structure stably as well as GCP-II gene.

According to the screening method of the invention, the reaction between GCP-II protein and a test subject can be confirmed by the conventional methods used to follow-up the reactions between protein-protein and protein-compound. For example, a method to measure the activity of the reaction product from the reaction between GCP-II gene or GCP-II protein and a test subject, yeast two-hybrid system, a method to detect phage-displayed peptide clone binding to GCP-II protein, high throughput screening (HTS) using natural or chemical library, drug hit HTS, cell-based screening or DNA microarray can be used.

By using one of these methods, the composition of the present invention can contains, in addition to a protein expressed from GCP-II, a buffer or reaction solution to maintain the structure or physiological activity of the protein. For the in vivo test, the composition of the present invention also includes cells expressing the protein or cells transfected with a vector expressing the protein in the presence of a promoter regulating transcription rate.

According to the screening method of the present invention, a test subject can be selected by the conventional selection method. So, a subject presumed to be functional as a preventive or therapeutic agent for Aβ accumulation in brain, an individual nucleic acid selected at random, a protein or other extracts or natural resources can be selected as a test subject.

Both a test subject proved to increase the expression of a gene or the function of the protein screened by the screening method of the invention and a test subject proved to inhibit the expression of the gene or the function of the protein can be candidates for a preventive and therapeutic agent for Aβ accumulation in brain by either being developed as a preventive and therapeutic agent for Aβ accumulation in brain (the former) or being developed as an inhibitor for the test subject (the latter). Such candidates for a preventive and therapeutic agent for Aβ accumulation in brain can act as a leading compound during the development processes of a preventive and therapeutic agent for Aβ accumulation in brain. And the structure of the leading compound can be modified and optimized in order to improve the functions of GCP-II gene or a protein expressed thereby, leading to the development of a novel preventive and therapeutic agent for Aβ accumulation in brain.

The leading compound above can inhibit Aβ accumulation in brain and diseases derived therefrom, which are caused by the inhibition of GCP-II gene expression or the decrease of the function of the protein expressed from GCP-II gene, since the compound can partially or fully increase the activity of the mammalian GCP-II gene or a protein expressed therefrom.

The present invention also provides a preventive and therapeutic agent for Aβ accumulation in brain containing an expression vector for GCP-II gene as an active ingredient.

In an exemplary embodiment of the invention, lenti-virus was used as a gene carrier for the intracellular transmission of GCP-II into cortical cells, but not always limited thereto. Particularly, to induce intracellular expression of GCP-II, retrovirus including adenovirus, adeno-associated virus, lenti-virus, etc. and vaccinia virus can be used.

BRIEF DESCRIPTION OF THE DRAWINGS

The application of the preferred embodiments of the present invention is best understood with reference to the accompanying drawings, wherein:

FIG. 1 is a set of graphs and photographs illustrating the degree of Aβ degradation in cells over-expressing GCP-II, which was compared with the degrees in cells over-expressing NEP (neprilysin) or ID (insulin degrading enzyme) E. FIG. 1A illustrates that synthetic Aβ$_{40}$ was introduced into HEK293 cells over-expressing GCP-II, NEP and IDE and upon completion of the reaction the remaining Aβ was quantified by ELISA assay kit (IBL), FIG. 1B illustrates that synthetic Aβ$_{42}$ was introduced into the same cells as the above and upon completion of the reaction the remaining Aβ$_{42}$ was quantified, and FIG. 1C is a set of photographs illustrating the expression levels of GCP-II and NEP in HEK293 cells by Western blot analysis using anti-GCP-II or anti-NEP antibody.

FIG. 2 is a graph illustrating the result of ELISA showing the level of Aβ degradation in cortical cells over-expressing GCP-II using lenti-virus.

FIG. 3 is a set of graphs showing the level of Aβ accumulated in cell culture medium with elimination of endogenous GCP-II, measured by RNAi method. FIG. 3A is a graph showing that the decrease of GCP-II expression in GCP-II knock-down stable cells was confirmed by RT-PCR using siGCP-II gene sequence and FIG. 3B is a graph showing that synthetic Aβ was introduced into siGCP-II knock-down stable cells and upon completion of the reaction the remaining Aβ was quantified by ELISA.

FIG. 4 is a set of a photograph and a graph showing the results of testing the recombinant II (referred as 'rGCP-II' hereinafter). FIG. 4A is a photograph showing that GCP-II was purified by using insect cells (Sf21), followed by coomassie staining and Western blotting and FIG. 4B is a graph showing Km value representing the enzyme activity of purified rGCP-II.

FIG. 5 is a set of graphs showing the amino acid sequence of rGCP-II responsible for the degradation of Aβ confirmed by MALDI-TOF. FIG. 5A is a graph illustrating the result of MALDI-TOF of Aβ, FIGS. 5B-5D are graphs illustrating the results of MALDI-TOF representing rGCP-II dependent Aβ$_{40}$ (100 ug/L) reactions, and FIG. 5E is a graph illustrating that boiled rGCP-II was reacted with Aβ$_{40}$, resulting in the confirmation that Aβ$_{40}$ degradation is related to the enzyme activity of rGCP-II.

FIG. 6 is a set of schematic diagrams showing the Aβ product generated by rGCP-II examined by MALDI-TOF.

FIG. 7 is a set of graphs showing the results of the interaction of rGCP-II with insulin β-chain, amylin and ACTH (Adrenocorticotropic Hormone) to examine the substrate specificity of rGCP-II. FIG. 7A is a graph showing the result of MALDI-TOF of insulin β-chain alone, FIG. 7B is a graph showing the result of MALDI-TOF of the mixture of rGCP-II and insulin β-chain, FIG. 7C is a graph showing the result of MALDI-TOF of ACTH alone, FIG. 7D is a graph showing the result of MALDI-TOF of a mixture of rGCP-II and ACTH, FIG. 7E is a graph showing the result of MALDI-TOF of amylin alone, and FIG. 7F is a graph showing the result of MALDI-TOF of a mixture of rGCP-II and amylin.

FIG. 8 is a set of a photograph and a graph showing the results of examination of endogenous Aβ degradation by rGCP-II. FIG. 8A is a photograph showing the APP expression level in Aβ over-producing $^{sw}$APP (Swedish mutant APP) over-expressing stable cell line and FIG. 8B is a graph showing the result of ELISA detecting the remaining Aβ in the cell culture medium after the reaction with rGCP-II.

FIG. 9 is a set of photographs and a graph showing that various forms of Aβ can be degraded by rGCP-II. FIG. 9A is a set of photographs showing the results of Western blot analysis examining rGCP-II dependent oligomer Aβ and monomer Aβ degradation and FIG. 9B is a graph showing the quantification of oligomer Aβ and monomer Aβ after 5 times of degradation tests, which was carried out by using an image analysis program based on the results of Western blot analysis.

FIG. 10 is a set of a graph and a schematic diagram showing the degradation of both soluble Aβ and insoluble Aβ by GCP-II. FIG. 10A is a graph showing the degradation of soluble Aβ and insoluble Aβ and FIG. 10B is a schematic diagram showing the degradation of soluble Aβ and insoluble Aβ by GCP-II.

FIG. 11 is a graph showing the result of Congo red assay measuring the level of aggregated Aβ after the reaction with rGCP-II.

FIG. 12 is a graph showing the result of Aβ degradation capacity by treating 2-PMPA that GCP-II inhibitor in over-expressing transgenic mouse and control. FIG. 12A is a graph showing the result of yield of $A\beta_{40}$ and $A\beta_{42}$ in cerebral cortex of over-expressing experiment and control by ELISA and FIG. 12B is a graph showing the result of change of GCP-II activity by 2-PMPA that GCP-II inhibitor in experiment and control.

MODE FOR THE INVENTION

Figures 6A, 6B:
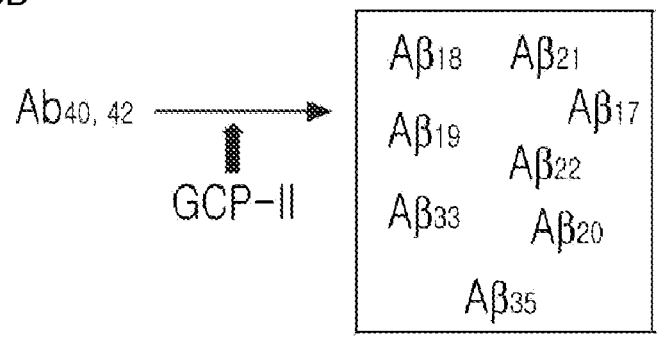
FIG. 6A shows the degradation site of Aβ by rGCP-II and FIG. 6B illustrates various degradation products of Aβ produced by GCP-II.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Investigation of Aβ Degradation Capacity of GCP-II

<1-1> GCP-II Obtainment

RT-PCR was performed to obtain human GCP-II cDNA. For the insertion into the vector pEF1/Myc (including Myc-tag at C-terminal, using BamH I and Not I restriction enzyme sites, Invitrogen, USA), PCR was performed with a forward primer represented by SEQ. ID. NO: 3 containing BamH I site and a reverse primer represented by SEQ. ID. NO: 4 and containing Not I site as follows.

Forward primer: cgcggatccaccatgtggaatctccttcacgaaa (SEQ ID NO: 3; GCP-II-1F)

Reverse primer: atttgcggccgctggctacttcactcaaagtctc (SEQ ID NO: 4; GCP-II-1R)

Forward primer: cgcagatctaccatgtggaatctccttcacgaaa (SEQ ID NO: 5; GCP-II-2F)

Reverse primer: atttagatctttaggctacttcactcaaagtctc (SEQ ID NO: 6; GCP-II-2R)

94° C. 5 min.
94° C. 30 sec., 62° C. 1 min., 72° C. 2 min.: 30 cycles
72° C. 7 min,
4° C.

To insert GCP-II cDNA into pSG5 (including HA tag at N-terminal, using Bgl II restriction enzyme site, Stratagene, USA), a forward primer represented by SEQ. ID. NO: 5 containing Bgl II site and a reverse primer represented by SEQ. ID. NO: 6 were used and PCR was performed under the same conditions as explained hereinbefore to amplify human GCP-II cDNA from human astrocyte U87 MG (ATCC, USA). The PCR product was inserted into each vector, which was named 'pMyc-GCPII' and 'pHA-GCPII' respectively.

Every clone used in the present invention was identified by DNA sequencing.

<1-2> Measurement of the Aβ Degradation Capacity of GCP-II

To measure the level of Aβ degradation by GCP-II, 2 ng/uL of synthetic $A\beta_{40}$ or $A\beta_{42}$ (Biosource international INC.) was added to HEK293 cell culture medium. Twenty hours later, the remaining Aβ in the medium was quantified by ELISA kit (Biosource international INC.).

HEK293 cells (human embryonic kidney cells) over-expressing GCP-II were temporarily transfected with GCP-II expression vector 'pHA-GCPII' or 'pmyc-GCPII' prepared in the above Example <1-1>, by using a transfection reagent (Lipofectamine Plus™ Reagent, Invitrogen, USA). The HEK293 cells with the temporary insertion of GCP-II were cultured in DMEM (Dulbecco's modified Eagle's medium) supplemented with 10% FBS (fetal bovine serum), 100 IU/ml of penicillin and 100□/ml of streptomycin. Cell lysate was obtained from the HEK293 cells by using RIPA buffer containing a protease inhibitor (aprotinin, leupeptin or phenylmethyl sulfonyl fluoride), and GCP-II protein was separated with 8% SDS-PAGE to examine the expression of GCP-II.

NEP and IDE genes inserted in pcDNA vector were respectively obtained from Professor Saito in Japan (Shipp et al., 1988, Proc, Natl, Acad, Sci., 85, 4819-23) and Professor Selkoe in USA (Kuo et al., 1991, Mol. Endocrinol., 5, 1467-76). And the vector containing those genes was temporarily introduced into HEK293 cells and the expressions of those genes in the cells were confirmed.

HEK293 cells transfected with NEP and IDE plasmids were used as a positive control and the cells transfected with mock vector were used as a negative control. The expressions of human GCP-II and NEP in the transfected HEK293 cells were investigated by Western blot analysis using anti-GCP-II antibody (MAB544B, Maine Biotechnology) or anti-NEP antibody (L-CD10-270, Novocastra) respectively (FIG. 1C).

The level of Aβ remaining in the culture medium of HEK293 cells expressing GCP-II was reduced to 60±5% 20 hours after the addition of Aβ compared with that in the medium of cells transfected with mock vector, suggesting that the effect of Aβ degradation capacity of GCP-II is similar to that of NEP or IDE, known as an Aβ degrading enzyme.

Example 2

Aβ Degradation in Cortical Cells Over-Expressing GCP-II by Lenti-Virus

To investigate whether the expression of GCP-II can degrade Aβ in cortical cells, GCP-II was over-expressed in the primary cortical cells by using lenti-virus, followed by investigation of Aβ degradation (FIG. 2). The primary cortical cells were separated and cultured from E16 rats (Sprague-Dawley rats). To prevent non-neuronal cells, which took less than 10% in the culture cells, from spreading, the cells were transferred and further cultured in a 24 well plate ($1\times10^5$ cells/well) containing 5-fluoro-2-deoxyuridine from the 3-6 days after the first culture. To prepare lenti-virus expressing GCP-II, GCP-II was inserted into pLentiH1.2 vector (named 'pLentiH1.2-GCPII', which was then introduced into 293T cells along with pLentiH1.2-GCP-II and packaging construct and envelope construct. Forty eight hours later, the concentration of the virus released in the medium was measured.

Accordingly, a lenti-virus gene carrier with the insertion of GCP-II was constructed, which was named 'Lenti-GCP-II'.

The primary cortical cells were infected with Lenti-GCP-II for three days, to which $A\beta_{40}$ was added for 20 hours. Then, the level of Aβ remaining in the medium was measured by ELISA as explained in Example 1.

The expression of GCP-II in the infected cells was investigated by Western blot analysis using anti-GCP-II antibody (MAB544B, Maine Biotechnology).

In the primary cortical cells infected with Lenti-GCP-II by 10, 20 and 50 MOI (multiplicity of infection), the Aβ was reduced approximately 90% (FIG. 2). The result indicates that GCP-II can efficiently degrade Aβ in cortical cells where Aβ is accumulated to cause AD.

Example 3

Examination of Aβ Degradation Capacity of GCP-II by RNAi Method at Physiological Level To investigate whether GCP-II is able to degrade not only synthetic Aβ in cultured cells over-expressing GCP-II but also endogenous Aβ physiologically, the present inventors prepared GCP-II knock-down stable cells by inhibiting the expression of GCP-II in HEK293 cells by means of siRNA method and then added synthetic Aβ thereto. Sixteen hours later, Aβ remaining unreacted in the medium was quantified by ELISA (FIG. 3). Aβ neomycin-resistant construct harboring GCP-II siRNA composed of 26 nucleotide sequences was purchased from Open Biosystems, which was then introduced into HEK293 cells. 600□/mL of G418 was used for the selection, leading to the preparation of GCP-II knock-down stable cells. RT-PCR was performed to confirm siGCP-II effect. Compared with the effect of siGCP-II in a control group expressing GCP-II harboring mock vector, siGCP-II reduced the expression of GCP-II in GCP-II knock-down stable cells (FIG. 3A), in particular the expression of GCP-II was significantly reduced in colonies #4-5 and #4-7 among HEK293 cell colonies.

Aβ was added to each cell culture medium, followed by culture for 20 hours. And the levels of Aβ remaining unreacted in each medium were compared. As a result, the amount of Aβ in GCP-II knock-down stable cells was approximately 1.7-2 times higher than that in stable cells expressing GCP-II harboring mock vector (FIG. 3B).

As shown hereinabove, Aβ degradation in cell culture medium wherein GCP-II expression was inhibited by siRNA cell line was reduced more than in a control, suggesting that GCP-II can reduce Aβ physiologically.

Example 4

Investigation of Aβ Degradation Capacity of GCP-II Using rhGCP-II

<4-1> Preparation of rGCP-II

To confirm whether the reduced level of Aβ in GCP-II over-expressing cells was attributed to the action of GCP-II and to locate the amino acid site of Aβ degraded by GCP-II, rGCP-II protein was prepared.

PCR was performed by using pEF-GCP-II prepared in Example 1 as a template and the PCR product was digested with restriction enzymes Bam HI and Xho I, which was then sub-cloned into the restriction enzyme sites of Bam HI and Xho I of pEntrBHRNX vector, a baculovirus vector (Neurogenex Co., Korea). The resultant vector was named 'pBHRNX-GCP-II'.

An insect cell line SF21 (Neurogenex Co., Korea) was used as a host cell line. 0.1 mM of IPTG was added to the insect cells infected with pBHRNX-GCP-II to induce the expression of a target protein.

The cells were resuspended in lysis buffer (50 mM $NaH_2PO_4$, pH 8.0, 300 mM NaCl, 10 mM imidazole, 1 mg/ml lysozyme, protease inhibitor cocktail), followed by sonification in ice. Centrifugation was performed to obtain pellet. The pellet was reacted with 1 ml of 50% Ni-NTA slurry and applied to protein purification column (His-Strep Ni-chelating column, Qiagen, USA), followed by washing three times with washing buffer (50 mM $NaH_2PO_4$, pH 8.0, 300 mM NaCl, 20 mM imidazole). At last, rGCP-II was eluted by using elution buffer (50 mM $NaH_2PO_4$, pH 8.0, 300 mM NaCl) and the protein expression was investigated by coomassie staining or Western blot analysis (FIG. 4A).

<4-2> Degradation Sites of Aβ by rGCP-II

Prior to the confirmation of the effect of rGCP-II on Aβ degradation, [$^3$H] glutamate separated from 0.002-2 μM N-acetyl-L-aspartyl-L-[3,4-$^3$H]-glutamate by 50 ng/μM of rGCP-II at 37° C. was measured to calculate Km value presenting the enzyme activity of rGCP-II. The enzyme activity of rGCP-II was saturated from 1.0 μM of N-acetyl-L-aspartyl-L-[3,4-$^3$H] and as a result, the Km value of rGCP-II was determined to be 0.5 μM.

After measuring the enzyme activity (Km=0.5 μM, FIG. 4B), $Aβ_{40}$ (100 ng/L) and GCP-II protein were reacted for 20 hours and peptides degraded therefrom were investigated by MALDI-TOF (matrix assisted laser desorption/ionization time of elight) (FIGS. 5A-5D). Aβ co-cultured with rGCP-II was loaded on the sample probe, and then dried at room temperature. The probe was put in the MALDI-TOF molecular weight analyzer (Vayager-DE Pro mass spectrometer, Applied Biosystems, USA) and the molecular weight of the sample was measured to determine the molecular weight of Aβ. Aβ was also reacted with inactivated GCP-II by heating. As a result, it was confirmed that Aβ was not degraded by the inactivated GCP-II (FIG. 5E).

A main peak was observed at 4331 in Aβ not-reacted with GCP-II, whereas two new peaks were observed at 3915 and 2662 in Aβ reacted with 0.5 ng/μM of GCP-II. The molecular weights corresponding to these peaks were consistent with the sizes of $Aβ_{35}$ and $Aβ_{21}$ peptides, indicating that these are the products from Aβ degradation by GCP-II. When the concentration of GCP-II was increased to 25 ng/μL, 6-7 new peaks were generated at 2,300 3,500. However, the concentration of GCP-II was raised to more than 25 ng/μL, only one peak was observed at 2,167 which corresponds to $Aβ_{18}$ and no more peptide fragments degraded by GCP-II were observed even with the further increase of the GCP-II concentration. Aβ degradation sites were determined by MALDI-TOF (FIG. 6A), suggesting that the major Aβ fragment degraded by GCP-II is $Aβ_{18}$ (FIG. 6B).

<4-3> Confirmation of GCP-II Specificity to Aβ

To investigate whether GCP-II degrades Aβ specifically, GCP-II was reacted with amylin and ACTH (adrenocorticotropic hormone) or insulin β-chain at 37° C. for 15 hours, followed by measuring the molecular weight of each sample with a molecular weight analyzer (FIG. 7). Insulin β-chain (FIGS. 7A and 7B) and ACTH (FIGS. 7C and 7D) were characteristically not degraded by GCP-II, whereas amylin showed two peaks at 1500 and 2000 after being reacted with GCP-II (FIGS. 7E and 7F).

Amylin is a protein that is aggregated in kidney to induce amyloidogenesis. Thus, from the above results, it was confirmed that GCP-II has a substrate specificity particularly to amyloidogenic proteins such as Aβ or amylin. According to the previous reports, IDE is also believed to degrade amylin (Benett, et al., J. Biol. Chem., 275, 36621-5, 2000). Thus, the capacity to degrade amylin of GCP-II suggests that GCP-II is a critical enzyme which can degrade a substrate having aggregation toxicity.

Example 5

Degradation of Endogenous Aβ by GCP-II

To investigate whether human GCP-II can actually degrade endogenous Aβ a cell line stably expressing $^{sw}$APP (Swedish mutant APP) gene involved in the over-production of Aβ was constructed. For this construction, $^{sw}$APP was introduced into HEK293 cells, followed by selection with G418. The recovered medium was reacted with rGCP-II protein and then Aβ remaining unreacted in the medium was quantified by ELISA (FIG. 8).

The concentration of $Aβ_{42}$ and the expression level of APP were used as standards for the selection of $^{sw}$APP stable cell colonies. Among the selected colonies, #2 colony exhibited the highest APP expression level (FIG. 8A) and 14-fold higher Aβ$_{42}$ concentration, compared with endogenous Aβ level. #2 colony of $^{sw}$APP stable cell colonies was co-cultured respectively with 0, 0.5, 2.5 and 10□/μL of rGCP-II. As a result, the level of endogenous Aβ$_{42}$ was decreased. From the above result, it was confirmed that rGCP-II is able to degrade physiologically generated (endogenous) Aβ alike (FIG. 8B).

Example 6

Degradation of Aβ Monomer and Multimer by GCP-II

To investigate the degradation effect of GCP-II on Aβ monomer and multimer, Aβmatured for 7 days was reacted with rGCP-II for 20 hours, followed by electrophoresis on 16% tris-tricine gel. Western blotting was performed using anti-Aβ antibody (6E10) more than 5 times (FIG. 9A) and the results were quantified by an image program (Image J program, NIH, USA) (FIG. 9B). As a result, when Aβ was reacted with GCP-II with increasing the GCP-II concentration, Aβ in oligomer form (multimer) was reduced faster than Aβ monomer. The above result indicates that GCP-II can efficiently degrade Aβ in oligomer form, which is known to be harmful for nerve cells, rather than Aβ monomer.

Example 7

Degradation Effect of GCP-II on Soluble Aβ and Insoluble Aβ

Considering that various forms of Aβ$_{40}$ were included in the reaction solution, the present inventors investigated the affinity of rGCP-II to Aβ$_{40}$ (FIG. 10).

The cerebral cortex was homogenized in 50 mM Tris-HCl (TBS) containing protease inhibitor cocktail (pH 7.6), followed by centrifugation at 4° C. with 100,000 g for 40 minutes. The supernatant was defined as a soluble fragment. The pellet was sonicated in 6 M guanidine-HCl solution containing protease inhibitor cocktail, which was defined as an insoluble fragment. The concentrations of each soluble Aβ and insoluble Aβ were measured.

The soluble Aβ or insoluble Aβ was co-cultured with rGCP-II. As a result, rGCP-II reduced insoluble Aβ$_{40}$ by 35% and soluble Aβ$_{40}$ by 20% (FIG. 10A). From the above results, it was confirmed that GCP-II of the present invention has degradation activity to not only soluble Aβ but also insoluble Aβ suggesting that GCP-II can degrade the aggregated Aβ more efficiently (FIG. 10B).

Example 8

Degradation Effect of rGCP-II on the Aggregated Aβ

Aβ was aggregated for 21 days, which was then reacted with rGCP-II protein for 16 hours. Then, the aggregated Aβ was quantified by Congo red assay to examine the degradation activity of rGCP-II.

5 μM Congo red solution (5.0 mM KH$_2$PO$_4$, 150 mM NaCl, pH 7.4) was prepared using 5.0 mM Congo red stock solution. Aβ was added thereto in the presence or absence of rGCP-II, which was cultured at room temperature for 30 minutes to obtain spectrum before measuring the absorption rate. In Congo red assay, the aggregated protein raises absorption spectroscopy by binding to Congo red.

The congo red value (Cb) of Aβ$_{40}$ aggregates matured for 21 days was 3±0.45 μM, but when the aggregates were reacted with GCP-II at different concentrations, Cb values were reduced respectively to 2.35, 1.82 and 0.72 with the increase of GCP-II concentration.

Under the action of rGCP-II, the Cb value of Aβ$_{18}$, a major Aβ fragment, was blank even after 21-day maturation. The above result indicates that only Aβ$_{40}$ is degraded by rGCP-II and as a result an Aβ fragment which lost aggregation core sequence is produced thereby.

Therefore, GCP-II of the present invention was proved to reduce Cb value dose-dependently and degrade various forms of Aβ in particular, aggregated Aβ more efficiently (FIG. 11).

Example 9

Investigation of Aβ Degradation Capacity by GCP-II Inhibitor

To conform whether GCP-II can actually degrade over-expressing Aβ in vivo, the present inventors investigated Aβ degradation capacity by GCP-II inhibitor in a transgenic mouse over-expressing these Aβ. Concretely, after prepared genetically Aβover-expressing dementia model mouse (APP Swdish/presenilin delta 9 deltion, 12 weeks, The Hackson Laboratory, USA), injected into visceral cavity twice in a week, dosage of 10 mg/kg, 30 days. At this time, PBS used as a control. After finally injected GCP-II inhibitor, cerebral cortex, hippocampus and cerebellum in mouse brain was dissected and measured their weight respectively using microblance. And then, the above tissues were incubated in 6 M guanidine-hydrochrolide solution, room temperature, 4 hours and obtained supernatant by centrifugation after added iced PBS at 1/10 ratio. The obtained sample were diluted appropriately concentration for ELISA measurement and were reacted for 3 hours after mixture with Aβ standard appropriately ratio added in Aβ antibody coating plate. Then treated HRP (horseradish peroxidase) tagging secondly actibody, the above reactant was measured absorbance at 450 nm wavelength after treated stained using TMB (tetramethylbensidine). To conform whether GCP-II inhibitor was treated correctly, a part of the above mouse brain tissue were dissected and detected GCP-II activaty. Concretely, the cell membrane layer existed GCP-II was isolated from the mouse brain tissue, the supernatant was obtained by untracentrifuge at 1,000,000 g after sonicating in 50 mM Tris-HCl soluation. 10□ protein in the obtained cell membrant layer was mixed with isopote ($^3$H) tagging NAAG (N-acetyl-aspartydyl-glutamate) and was incuvated at 37° C. and centrifuged at 1,000 g through 96-well spin column filled AG-1X8 anion exchange resion and isolated brokon glutamate by GCP-II using 0.5 M formate. In this manner, isolated sample were measured GCP-II activity using isotope meter.

As FIG. 12A, the result of yield of Aβ$_{40}$ and Aβ$_{42}$ in cerebral cortex of experiment and control mouse by measured ELISA was showing the yield of Aβ$_{40}$ existed in cerebral cortex tissue of transgenic mouse and control has no significantly difference in the statistics, the yield of and Aβ$_{42}$ was increased about 30% in experiment more then control. At this time, Aβ$_{40}$ and Aβ$_{42}$ were almost not detected in wild type mouse. And 2-PMPA treated in dementia model mouse can inhibit GCP-II activaty was investigated and as a result, GCP-II was significantly degraded about 50% in wild type mouse and about 30% in transgenic mouse. As show hereinabove, suggesting that GCP-II inhibitor reduce GCP-II activity in brain.

Therefore, when GCP-II activity reduce by 2-PMPA that GCP-II inhibitor, from the above, reduced Aβ degradation by GCP-II, as a result the yield of A$\beta_{42}$ is induced. In other word, this is important result is showing GCP-II involve A$\beta$ degradation in brain.

INDUSTRIAL APPLICABILITY

As explained hereinbefore, a novel protease GCP-II can degrade various forms of A$\beta$ including A$\beta$ monomer and oligomer, soluble A$\beta$ and insoluble A$\beta$ and particularly aggregated A$\beta$ so that it can be effectively used for the development of a therapeutic agent for AD, Down's syndrome and amyloidosis and for the gene therapy as well.

Sequence Listing

SEQ. ID. NO: 1 is a nucleotide sequence encoding human GCP-II.

SEQ. ID. NO: 2 is an amino acid sequence encoding human GCP-II.

SEQ. ID. NO: 3 is the sequence of a forward primer used for PCR for cloning human GCP-II cDNA into pEF1/Myc vector.

SEQ. ID. NO: 4 is the sequence of a reverse primer used for PCR for cloning human GCP-II cDNA into pEF1/Myc vector.

SEQ. ID. NO: 5 is the sequence of a forward primer used for PCR for cloning human GCP-II cDNA into pSG5 vector.

SEQ. ID. NO: 6 is the sequence of a reverse primer used for PCR for cloning human GCP-II cDNA into pSG5 vector.

The Sequence Listing is submitted as an ASCII text file in the form of the file named Sequence_Listing.txt, which was created on May 18, 2010, and is 11,335 bytes, which is incorporated by reference herein.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for inhibiting β-amyloid (Aβ) accumulation in vitro, comprising:
   contacting Aβ with a glutamate carboxypeptidase-II (GCP-II) protein or a cell comprising a recombinant expression vector comprising a polynucleotide encoding the GCP-II protein.

2. The method according to claim 1, wherein the GCP-II protein has an amino acid sequence represented by SEQ. ID. NO: 2.

3. The method according to claim 1, wherein the polynucleotide encoding the GCP-II protein has a nucleic acid sequence represented by SEQ. ID. NO: 1.

4. The method according to claim 1, wherein the Aβ is soluble Aβ or insoluble Aβ.

5. The method according to claim 1, wherein the expression vector is selected from the group consisting of adenovirus, adeno-associated virus, lentivirus, retrovirus, and vaccinia virus.

* * * * *